US007678901B2

(12) United States Patent
Zhao (10) Patent No.: US 7,678,901 B2
(45) Date of Patent: Mar. 16, 2010

(54) RAPAMYCIN ANALOGS CONTAINING AN ANTIOXIDANT MOIETY (75) Inventor: Jonathon Z. Zhao, Belle Mead, NJ (US)

(73) Assignee: Wyeth, Madison, NJ (US)

(*) Notice: Subject to any disclaimer, the term of this patent is extended or adjusted under 35 U.S.C. 154(b) by 164 days.

(21) Appl. No.: 11/364,446

(22) Filed: Feb. 28, 2006

(65) Prior Publication Data
US 2007/0203170 A1 Aug. 30, 2007

(51) Int. Cl.
C07D 498/18 (2006.01)
(52) U.S. Cl. .................................... 540/456
(58) Field of Classification Search ................ 540/456; 514/291
See application file for complete search history.

(56) References Cited

U.S. PATENT DOCUMENTS

| | | | |
|---|---|---|---|
| 3,929,992 | A | 12/1975 | Sehgal et al. |
| 3,993,749 | A | 11/1976 | Sehgal et al. |
| 4,316,885 | A | 2/1982 | Rakhit |
| 4,401,653 | A | 8/1983 | Eng |
| 4,650,803 | A | 3/1987 | Stella et al. |
| 4,885,171 | A | 12/1989 | Surendra et al. |
| 5,023,262 | A | 6/1991 | Caufield et al. |
| 5,120,725 | A | 6/1992 | Kao |
| 5,120,727 | A | 6/1992 | Kao et al. |
| 5,120,842 | A | 6/1992 | Failli et al. |
| 5,177,203 | A | 1/1993 | Failli et al. |
| 5,310,901 | A | 5/1994 | Parsons et al. |
| 5,385,908 | A | 1/1995 | Nelson et al. |
| 5,457,111 | A | 10/1995 | Luly et al. |
| 5,491,231 | A | 2/1996 | Nelson et al. |
| 5,672,605 | A | 9/1997 | Or et al. |
| 6,015,815 | A | 1/2000 | Mollison et al. |

FOREIGN PATENT DOCUMENTS

| | | |
|---|---|---|
| EP | 0467606 A1 | 1/1992 |
| EP | 184162 B1 | 11/2006 |
| FR | 900.520 | 12/1943 |
| FR | 900.523 | 12/1943 |
| FR | 900.525 | 12/1943 |
| WO | WO 92/05179 A1 | 4/1992 |
| WO | WO 94/09010 A | 4/1994 |

OTHER PUBLICATIONS

Chen, Yanqui, et al. "Synthesis and Bioactivity of Photolabile Sirolimus (Rapamycin) Analogs" Bioorganic and Medicinal Chemistry Leters, vol. 5, No. 13, Jul. 6, 1995.
Fretz, H. et al. "Rapamycin and FK506 Binding Proteins (Immunophilins)" Jurnal of the American Chemical Society, American Chemil Socieity, vol. 113, No. 4, Feb. 13, 1991.
European Search Report dated Jun. 27, 2007 for Application No. 07250712.2-1211.
Bierer, B.E., et al. "The Effect of the Immunosupprssant FK-06 on Alternate Pathways of T Cell Activation", Eur. J. Immunol. 1991, 439-445.
Brown, E.J., et al. "A Mammalian Protein Targeted by G1-Arreting Rapamycin-Receptor Complex," Letters to Nature, vol. 369, p. 756.
Dumont, F.J., et al. "The Immunosuppressive Macrolides FK-506 and Rapamycin Act as Reciprocal Antagonists in Murine T Cells", Journal of Immunology, vol. 144, No. 4, 1990, pp. 1418-1424.
Fretz, H., et al. Rapamycin andFK506 Binding Proteins (Immunophilins), J. Am. Chem. Soc. 1991, vol. 113, pp. 1409-1411.
Hayward, C.J., et al. "Total Synthesis of Rapamycin via a Novel Titanium-Mediated Aldol Macrocycliation Reaction", J. Am. Chem. Soc. 1993, ol. 115, pp. 9345-9346.
Nicolaou, K.C., et al. "Total Synthesis of Rapamycin", J. Am. Chem. Soc. 1993, vol. 115, pp. 4419-4420.
Paiva, N.L., et al. "Incorporation of Acetate, Propionae, and Methionine Into Rapamycin by *Streptomyces hygrosscopicus*", Journal of Natural Products, vol. 54, No. 1, pp. 167-177,1991.
Romo, D., et al. "Total Synthesis of (-) Rapamycin Using an Evans-ischenko Fragment Coupling", J. Am. Chem. Soc. 1993,vol. 115, pp. 7906-7907.
Sabatini, D.M, et al. "Raft1: A Mammalian Protein That Binds to FKBP 12 in a Rapamycin-Dependent Fashion and is Homologous to Yeast TORs", Cell, vol. 78, 1994, pp. 35-43.
Siekierka, J.J, et al. "A Cyosolic Binding Protein for the Immunosuppressant FK506 Has Peptidyl-Propyl Isomerase Activity but is Distinct from Cyclophilin", Letters to Nalture, vol. 341, 1989, p. 755.
H.A. Baker et al., *Rapamycin (AY-22,989), A New Antifungal Antibiotic III. In Vitro And in Vivo Evaluation*, J. Antibiot., 31, 6, 539-545, 1978.
T.E. Bunchman and C.A. Brookshire, *Smooth Muscle Cell Proliferation by Conditioned Media From Cyclosporine-Treated Endothelial Cells: A Role of Endothelin*, Transplantation Proceed. 23, No. 1, 967-968, 1991.
S. J. Danishefsky, Cheryl M. Hayward, et al., J. Am. Chem. Soc., *Total Synthesis of rapamycin via a novel titanium-mediated aldol macrocyclization reaction*, 115 (20), 9345-9346, 1993.
Galat, A., Harding, M.W., Uehling, D.E., Schreiber, S.L., *A receptor for the immune-suppressant FK506 is a cis-trans peptidyl-prolyl isomerase*, Nature, 341, 758-760, 1989.
R. R. Martel et al., *Inhibition of the immune response by rapamycin, a new antifungal antibiotic*, Can. J. Physiol. Pharmacol., 55, 48-51, 1977.

(Continued)

Primary Examiner—Bruck Kifle
(74) Attorney, Agent, or Firm—Carl J. Evens (57) ABSTRACT A rapamycin analog with an antioxidant moiety or a pharmaceutically acceptable salt or prodrug thereof, is an immunomodulatory agent and is useful in the treatment of restenosis and immune and autoimmune diseases. Also disclosed are cancer-, fungal growth-, restenosis-, post-transplant tissue rejection- and immune- and autoimmune disease- inhibiting compositions and a method of inhibiting cancer, fungal growth, restenosois, post-transplant tissue rejection, and immune and autoimmune disease in a mammal. One particular preferred application of such antioxidant moiety containing rapamycin analog is in medicated devices wherein the stability and resistance to oxidative processes are essential to the success of rapamycin containing combination devices.

5 Claims, 6 Drawing Sheets

OTHER PUBLICATIONS

R. Morris, et al., *Identification of a new pharmacologic action for an old compound*, Med. Sci. Res., 17, 877-878, 1989.

D. M. Prescott, Ed., G. Poste, et al., *Lipid Vesicles as Carriers for Introducing Biologically Active Materials into Cells*, Methods in Cell Biology, vol. XIV, Academic Press, NY, NY p. 33 et seq., 1976.

S.L. Schreiber, D. Romo, et al., *Total Synthesis of (—) Rapamycin Using an Evans-Tishchenko Fragment Coupling*, J. Am. Chem. Soc., 115, 7906-7907, 1993.

S.N. Sehgal, C. Vezina, et al., *Rapamycin (AY-22,989), A New Antifungal Antibiotic II. Fermentation, Isolation and Characterization*, J. Antibiotics (Tokyo), 28, 10, 727-732, 1975.

S.N. Sehgal, H. Baker, C. Vezina, et al., *Demethoxyrapamycin (AY 24,668), A New Antifungal Antibiotic*, J. Antibiot. (Tokyo), 36(4), 351-354, 1983.

M. Shichiri, et al., *Endothelin-1 is an Autocrine/Paracrine Growth Factor for Human Cancer Cell Lines*, J. Clin. Invest. 87 1867-1871, 1991.

Vezina, C., A Kudelski & S.N. Sehgal, J. Antibiotics (Tokyo), Rapamycin (AY-22,989), a new antifungal antibiotic.I. Taxonomy of the producing streptomycere and isolation of the active principle, 28, 721-726, 1975.

Yamagishi, et al., *Endothelin 1 Mediates Endothelial Cell-Dependent Proliferation of Vascular Pericytes*, Biochem and Biophys. Res. Comm. 191, 3, 840-846, 1993.

RCOOH
DIC, DMAP, CH₂Cl₂
⟶
RT, 1-2 hr

RAPAMYCIN ANALOGS CONTAINING AN ANTIOXIDANT MOIETY

BACKGROUND OF THE INVENTION

1. Field of the Invention

The present invention relates to novel chemical compounds having an antioxidant moiety and having immunomodulatory activity and synthetic intermediates useful for the preparation of the novel compounds, and in particular to macrolide immunomodulators. More particularly, the present invention relates to semisynthetic analogs of rapamycin having an antioxidant moiety, means for their preparation, pharmaceutical compositions containing such compounds, and methods of treatment employing the same.

2. Discussion of the Related Art

The compound cyclosporine (cyclosporin A) has found wide use since its introduction in the fields of organ transplantation and immunomodulation, and has brought about a significant increase in the success rate for transplantation procedures. Recently, several classes of macrocyclic compounds having potent immunomodulatory activity have been discovered. Okuhara et al., in European Patent Application No. 184, 162, published Jun. 11, 1986, discloses a number of macrocyclic compounds isolated from the genus *Streptomyces*, including the immunosuppressant FK-506, a 23-membered macrocyclic lactone, which was isolated from a strain of *S. tsukubaensis*.

Other related natural products, such as FR-900520 and FR-900523, which differ from FK-506 in their alkyl substituent at C-21, have been isolated from *S. hygroscopicus yakushimnaensis*. Another analog, FR-900525, produced by *S. tsukubaensis*, differs from FK-506 in the replacement of a pipecolic acid moiety with a proline group. Unsatisfactory side-effects associated with cyclosporine and FK-506, such as nephrotoxicity, have led to a continued search for immunosuppressant compounds having improved efficacy and safety, including an immunosupressive agent which is effective topically, but ineffective systemically (U.S. Pat. No. 5,457,111).

Figure 1:
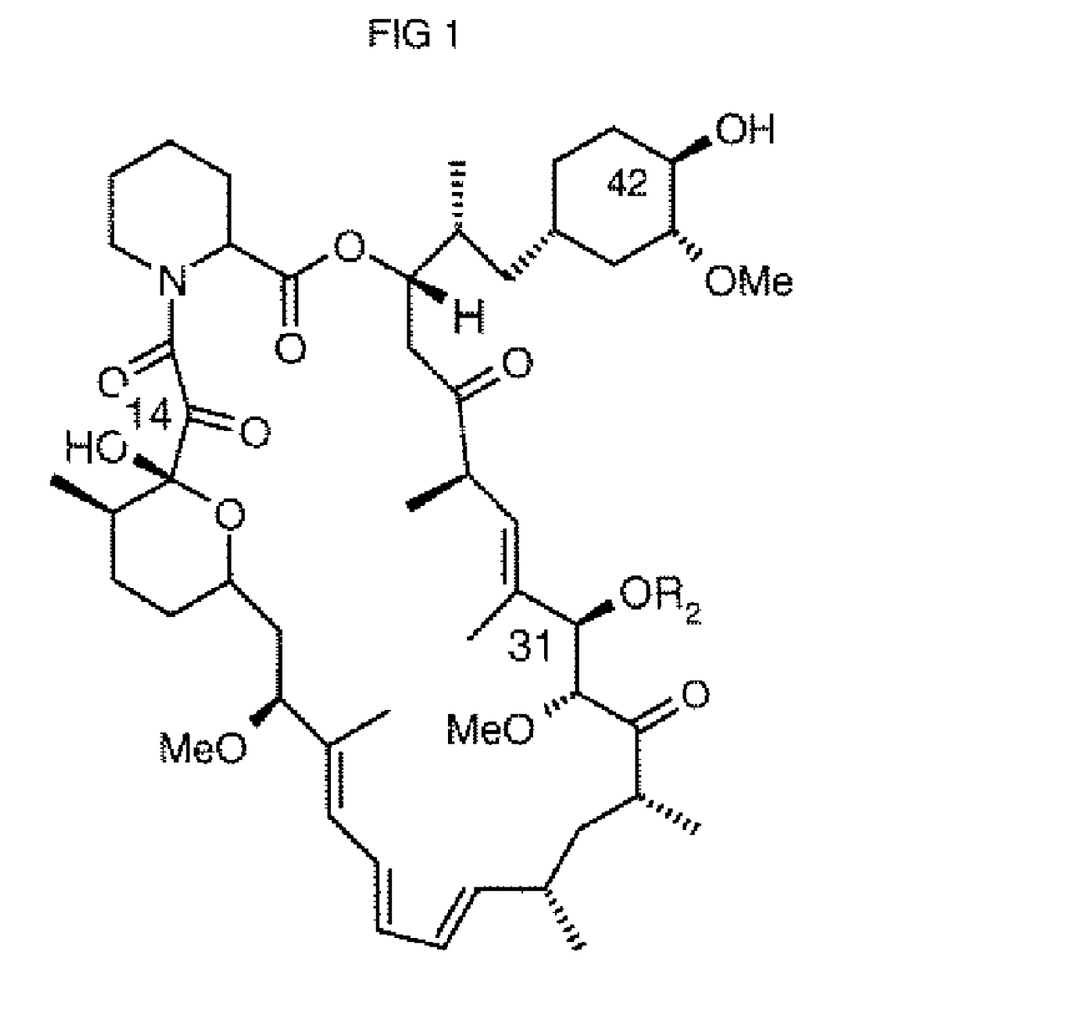
FIG. 1 illustrates a rapamycin structure in accordance with the present invention.

Rapamycin, as illustrated in FIG. 1, is a macrocyclic triene antibiotic produced by *Streptomyces hygroscopicus*, which was found to have antifungal activity, particularly against *Candida albicans*, both in vitro and in vivo (C. Vezina et al., J. Antibiot. 1975, 28, 721; S. N. Sehgal et al., J. Antibiot. 1975, 28, 727; H. A. Baker et al., J. Antibiot. 1978, 31, 539; U.S. Pat. No. 3,929,992; and U.S. Pat. No. 3,993,749).

FIG. 1 illustrates a rapamycin structure as produced from a fermentation process.

Rapamycin alone (U.S. Pat. No. 4,885,171) or in combination with picibanil (U.S. Pat. No. 4,401,653) has been shown to have antitumor activity. In 1977, rapamycin was also shown to be effective as an immunosuppressant in the experimental allergic encephalomyelitis model, a model for multiple sclerosis; in the adjuvant arthritis model, a model for rheumatoid arthritis; and was shown to effectively inhibit the formation of IgE-like antibodies (R. Martel et al., Can. J. Physiol. Pharmacol., 1977, 55, 48).

The immunosuppressive effects of rapamycin have also been disclosed in FASEB, 1989, 3, 3411, as has its ability to prolong survival time of organ grafts in histoincompatible rodents (R. Morris, Med. Sci. Res., 1989, 17, 877). The ability of rapamycin to inhibit T-cell activation was disclosed by M. Strauch (FASEB, 1989, 3, 3411). These and other biological effects of rapamycin are reviewed in Transplantation Reviews, 1992, 6, 39-87.

Mono-ester and di-ester derivatives of rapamycin (esterification at positions 31 and 42) have been shown to be useful as antifungal agents (U.S. Pat. No. 4,316,885) and as water soluble prodrugs of rapamycin (U.S. Pat. No. 4,650,803). Fermentation and purification of rapamycin and 30-demethoxy rapamycin have been described in the literature (C. Vezina et al. J. Antibiot. (Tokyo), 1975, 28 (10), 721; S. N. Sehgal et al., J. Antibiot. (Tokyo), 1975, 28(10), 727; 1983, 36(4), 351; N. L. Pavia et al., J. Natural Products, 1991, 54(1), 167-177).

Numerous chemical modifications of rapamycin have been attempted. These include the preparation of mono- and di-ester derivatives of rapamycin (WO 92/05179), 27-oximes of rapamycin (EPO 467606); 42-oxo analog of rapamycin (U.S. Pat. No. 5,023,262); bicyclic rapamycins (U.S. Pat. No. 5,120,725); rapamycin dimers (U.S. Pat. No. 5,120,727); silyl ethers of rapamycin (U.S. Pat. No. 5,120,842); and arylsulfonates and sulfamates (U.S. Pat. No. 5,177,203). Rapamycin was recently synthesized in its naturally occurring enantiomeric form (K. C. Nicolaou et al., J. Am. Chem. Soc., 1993, 115, 4419-4420; S. L. Schreiber, J. Am. Chem. Soc., 1993, 115, 7906-7907; S. J. Danishefsky, J. Am. Chem. Soc., 1993, 115, 9345-9346.

It has been known that rapamycin, like FK-506, binds to FKBP-12 (Siekierka, J. J.; Hung, S. H. Y.; Poe, M.; Lin, C. S.; Sigal, N. H. Nature, 1989, 341, 755-757; Harding, M. W.; Galat, A.; Uehling, D. E.; Schreiber, S. L. Nature 1989, 341, 758-760; Dumont, F. J.; Melino, M. R.; Staruch, M. J.; Koprak, S. L.; Fischer, P. A.; Sigal, N. H. J. Immunol. 1990, 144, 1418-1424; Bierer, B. E.; Schreiber, S. L.; Burakoff, S. J. Eur. J. Immunol. 1991, 21, 439-445; Fretz, H.; Albers, M. W.; Galat, A.; Standaert, R. F.; Lane, W. S.; Burakoff, S. J.; Bierer, B. E.; Schreiber, S. L. J. Am. Chem. Soc. 1991, 113, 1409-1411). Recently it has been discovered that the rapamycin/FKBP-12 complex binds to yet another protein, which is distinct from calcineurin, the protein that the FK-506/FKBP-12 complex inhibits (Brown, E. J.; Albers, M. W.; Shin, T. B.; Ichikawa, K.; Keith, C. T.; Lane, W. S.; Schreiber, S. L. Nature 1994, 369, 756-758; Sabatini, D. M.; Erdjument-Bromage, H.; Lui, M.; Tempest, P.; Snyder, S. H. Cell, 1994, 78, 35-43).

One recent example of a rapamycin analog is a tetrazole containing rapamycin analog (U.S. Pat. No. 6,015,815). The tetrazole heterocyclic ring is used to replace the hydroxyl group to effect the analog.

Although some of these modified compounds exhibit immunosuppressive activity, anti-restenotic activities in suppressing the migration and growth of vascular smooth muscles, especially when used in a stent coating, the need remains for rapamycin analogs which possess potentially enhanced resistance to oxidative forces and better stability in a formulation. One way to achieve the potentially enhanced antioxidant property is through a conjugation of one or more known antioxidant functional groups to the side chain of a rapamycin.

SUMMARY OF THE INVENTION

Accordingly, an object of the present invention is to provide novel semisynthetic rapamycin analogs which possess the desired antioxidant moiety attached to either or both of hydroxyl groups at 31-, and or 42-position of a rapamycin molecule.

Figure 2:
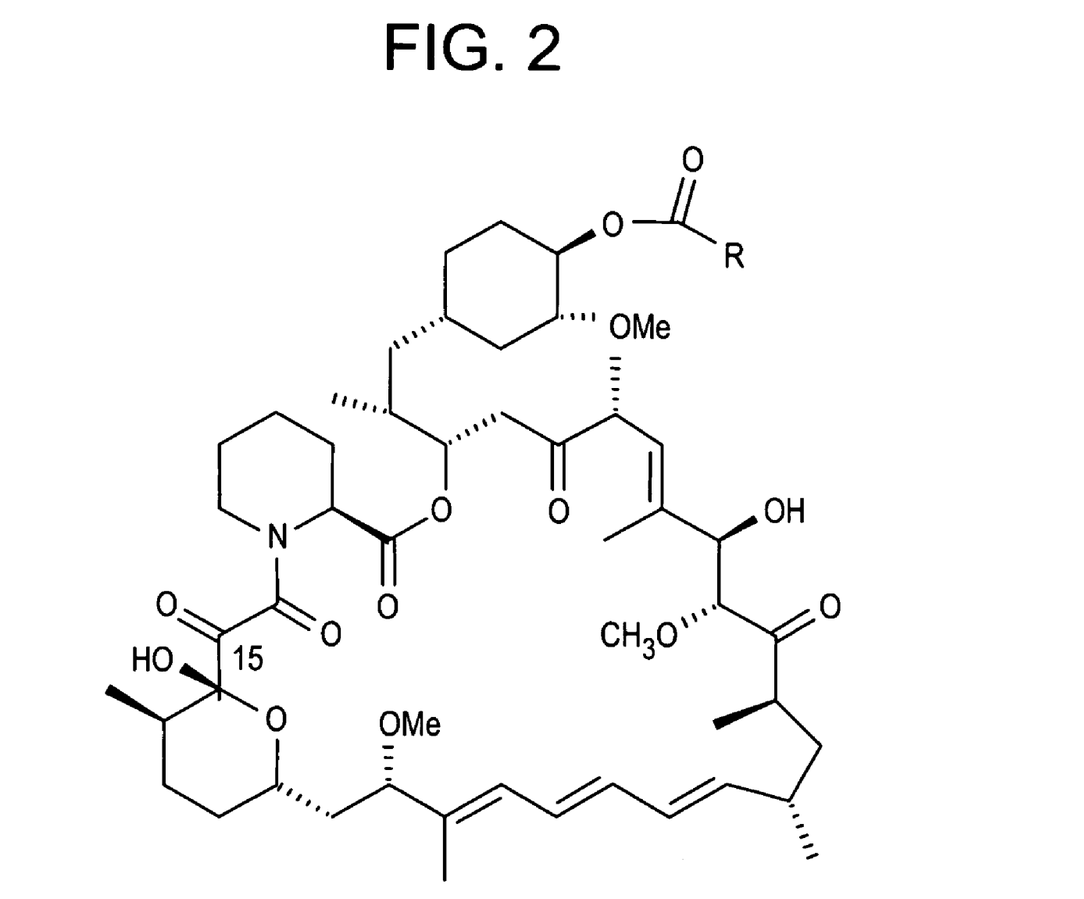
FIG. 2 illustrates a rapamycin analog containing an antioxidant moiety at 42-position in accordance with the present invention.

In accordance with one aspect, the present invention is directed to compounds represented by the structural formula illustrated in FIG. 2.

FIG. 2 represents a rapamycin analog with one antioxidant moiety at the 42-position, or a pharmaceutically acceptable salt or prodrug thereof, and where R is an organic moiety possessing antioxidant functions.

In accordance with yet another aspect, a compound of the present invention may contain two such substitutes at both the 42 and 31-positions of a rapamycin.

Figure 3:
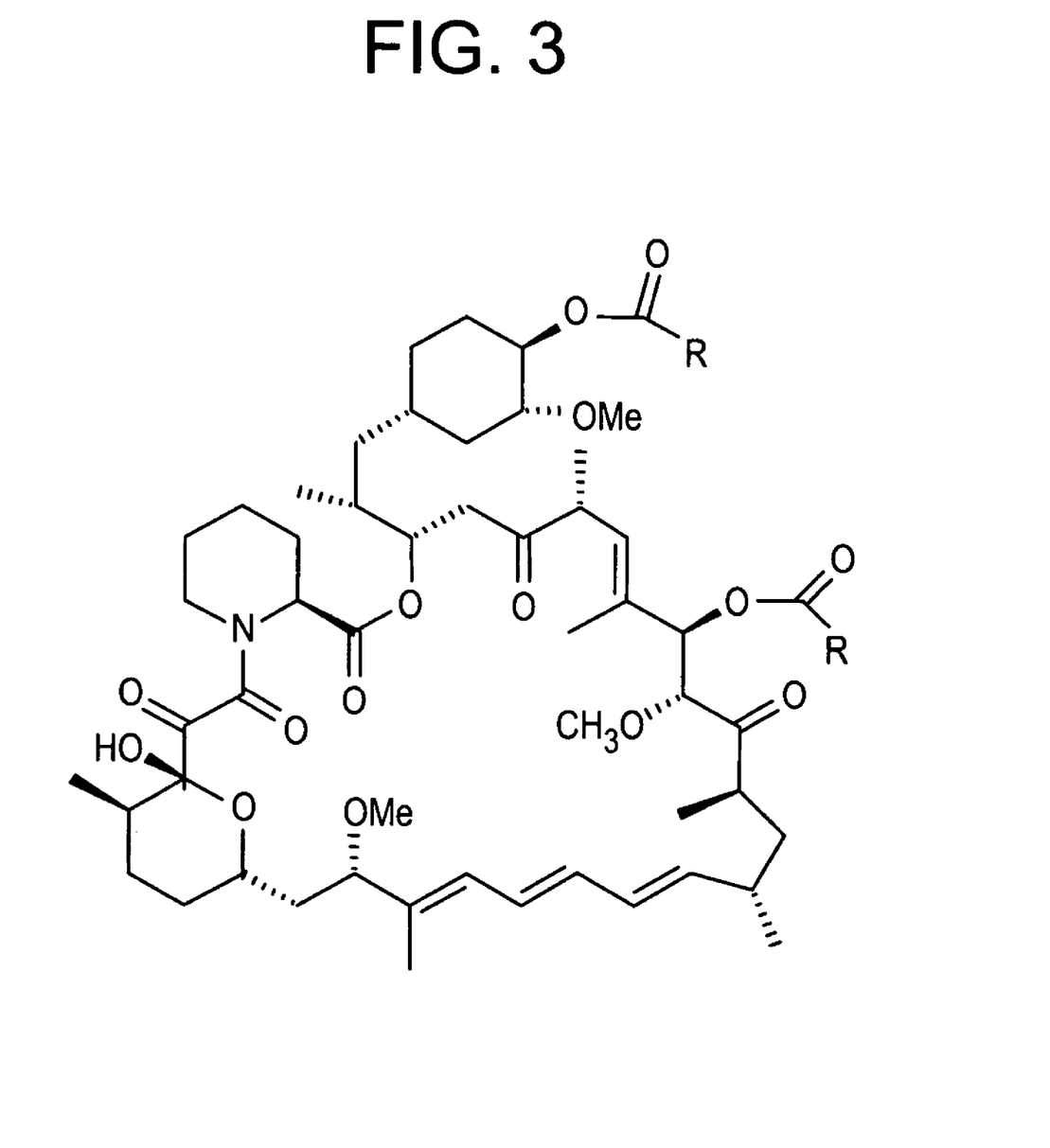
FIG. 3 illustrates a rapamycin analog containing an antioxidant moiety at both 42- and 31-positions in accordance with the present invention.

FIG. 3 illustrates a rapamycin analog with an antioxidant moiety at both the 42- and 31-positions, or a pharmaceutically acceptable salt or prodrug thereof, and where R is an organic moiety possessing antioxidant functions.

The antioxidant moiety of the present invention may be selected from naturally existing compounds such as polyunsaturated fatty acids (PUFA), with either conjugated or unconjugated polyene structures, possess 18, 20, 22 carbons, and 2-6 unconjugated cis-double bonds separated by one methylene, such as linolenic acid (LNA), linoleic acid (LA), arachidonic acid (AA), eicosapentaenoic acid (EPA), and docosahexaenoic acid (DHA). They and their metabolites are generally considered to be safe.

Other conjugated-polyenoic fatty acids, including, alpha- and beta-parinaric acid (combination of cis- and trans-tetraene component) may also be used to construct the antioxidant moiety of the present invention.

Similar conjugated polyunsaturated fatty acids may be synthesized for this particular purpose.

Similarly other protected and active forms of phenolic compounds such as tocopherol (vitamin E) and its many natural and synthetic derivatives may be conjugated to sirolimus and its many analogs with enhanced anti-oxidative properties.

Another object of the present invention is to provide a synthetic processes for the preparation of such compounds from starting materials obtained by fermentation, as well as chemical intermediates useful in such synthetic processes.

A further object of the present invention is to provide pharmaceutical compositions containing, as an active ingredient, at least one of the above compounds.

Yet another object of the present invention is to provide a method of treating a variety of disease states, including restenosis, post-transplant tissue rejection, immune and autoimmune dysfunction, fungal growth, and cancer.

In addition, the compounds of the present invention may be employed as a solution, cream, or lotion by formulation with pharmaceutically acceptable vehicles containing 0.1-5 percent, preferably 2 percent, of active compound which may be administered to a fungally affected area.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Definition of Terms

The term "prodrug," as used herein, refers to compounds which are rapidly transformed in vivo to the parent compound of the above formula, for example, by hydrolysis in blood. A thorough discussion is provided in T. Higuchi and V. Stella, "Pro-drugs as Novel Delivery Systems," Vol. 14 of the A.C.S. Symposium Series, and in Edward B. Roche, ed., "Bioreversible Carriers in Drug Design," American Pharmaceutical Association and Pergamon Press, 1987, both of which are hereby incorporated by reference.

The term "pharmaceutically acceptable prodrugs," as used herein, refers to those prodrugs of the compounds of the present invention which are, within the scope of sound medical judgment, suitable for use in contact with the tissues of humans and lower mammals without undue toxicity, irritation, and allergic response, are commensurate with a reasonable benefit/risk ratio, and are effective for their intended use, as well as the zwitterionic forms, where possible, of the compounds of the present invention. Particularly preferred pharmaceutically acceptable prodrugs of the present invention are prodrug esters of the C-31 hydroxyl group of compounds of the present invention.

The term "prodrug esters," as used herein, refers to any of several ester-forming groups that are hydrolyzed under physiological conditions. Examples of prodrug ester groups include acetyl, ethanoyl, pivaloyl, pivaloyloxymethyl, acetoxymethyl, phthalidyl, methoxymethyl, indanyl, and the like, as well as ester groups derived from the coupling of naturally or unnaturally-occurring amino acids to the C-31 hydroxyl group of compounds of the present invention.

The term "isomer" as used herein, refers to a compound having the identical chemical formula but different structural or optical configurations.

The term "epimer" as used herein, refers to a compound having the identical chemical formula but a different optical configuration at a particular position. In the case of a rapamycin, a 42-Epi rapamycin refers to the compound that has the opposite optical rotation compared to the rapamycin obtained by a fermentation process.

The term "15-isomer" as used herein, refers to the analog of rapamycin that contains a 7-member ring at the 15-position as opposed to a regular rapamycin obtained from a fermentation process which contains a six-member ring. This kind of conversion is also called "tautomerization". The I5-isomer" as used herein, may also be referred to as a 15 tautomer of a rapamycin.

Exemplary Structural Formulas

Figure 6:
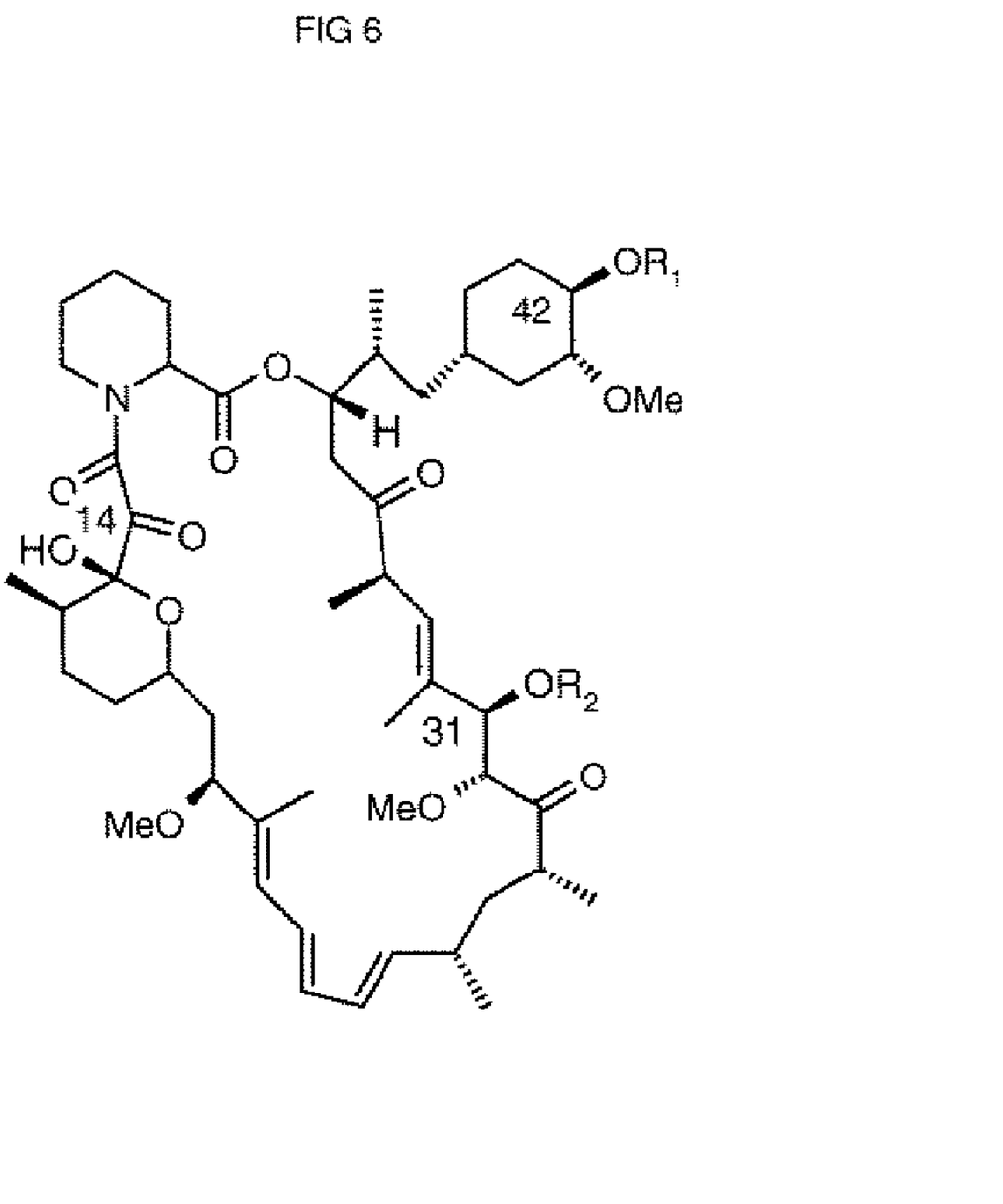
FIG. 6 illustrates an exemplary compound of the current invention which contains commonly known antioxidant functional groups such as conjugated polyunsaturated acids, a phenolic, a triazole, and a tetrazole.

In one exemplary embodiment of the present invention, there is a compound of the structural formula illustrated in FIG. 6, wherein R1 and R2 are each, independently, a hydrogen, or R3. R3 is an organic moiety that contains commonly known antioxidant functional groups such as conjugated polyunsaturated acids, a phenolic, a triazole, a tetrazole. The typical examples of these antioxidant functional moieties are set forth below.

FIG. 6 illustrates an exemplary compound of the current invention which contains commonly known antioxidant functional groups such as conjugated polyunsaturated acids, a phenolic, a triazole, a tetrazole at one or both of 42 and 31 positions on a rapamycin macrolide.

Preparation of Compounds

The compounds and processes of the present invention will be better understood in connection with the following synthetic schemes which illustrate the methods by which the compounds of the present invention may be prepared.

The compounds of the present invention may be prepared by a variety of synthetic routes. Most of the common conjugation reactions of rapamycin at 42- and/or 31-hydroxyl positions are found in previous rapamycin patents. A representative procedure is shown in FIG. 4.

Figure 4:
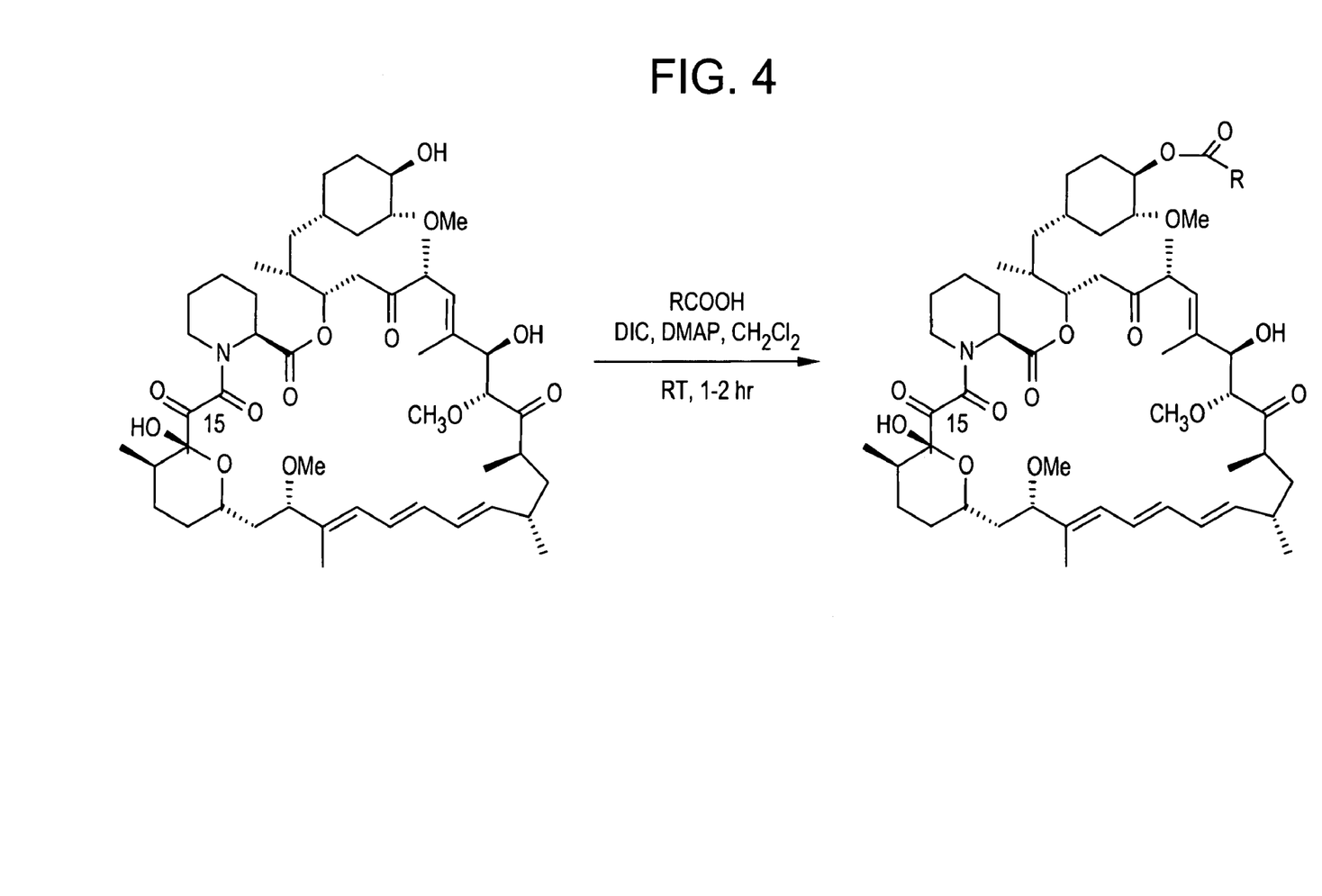
FIG. 4 illustrates an exemplary reaction scheme to introduce one antioxidant moiety at the 42-position of a rapamycin molecule in accordance with the present invention.

FIG. 4 illustrates a reaction scheme for mono-substituted rapamycin analog with one antioxidant moiety at the 42-position. R is an organic moiety possessing antioxidant functions as detailed below. Common conjugation reactions such as the ones listed in previous rapamycin patents may be used to effect the conjugation reaction. It is essential that the R domain contains an antioxidant function and the different components of R do not interfere with the conjugation reaction. A flash chromatography may be needed to separate the mono-substituted rapamycin analog from the di-substituted analog.

Figure 5:
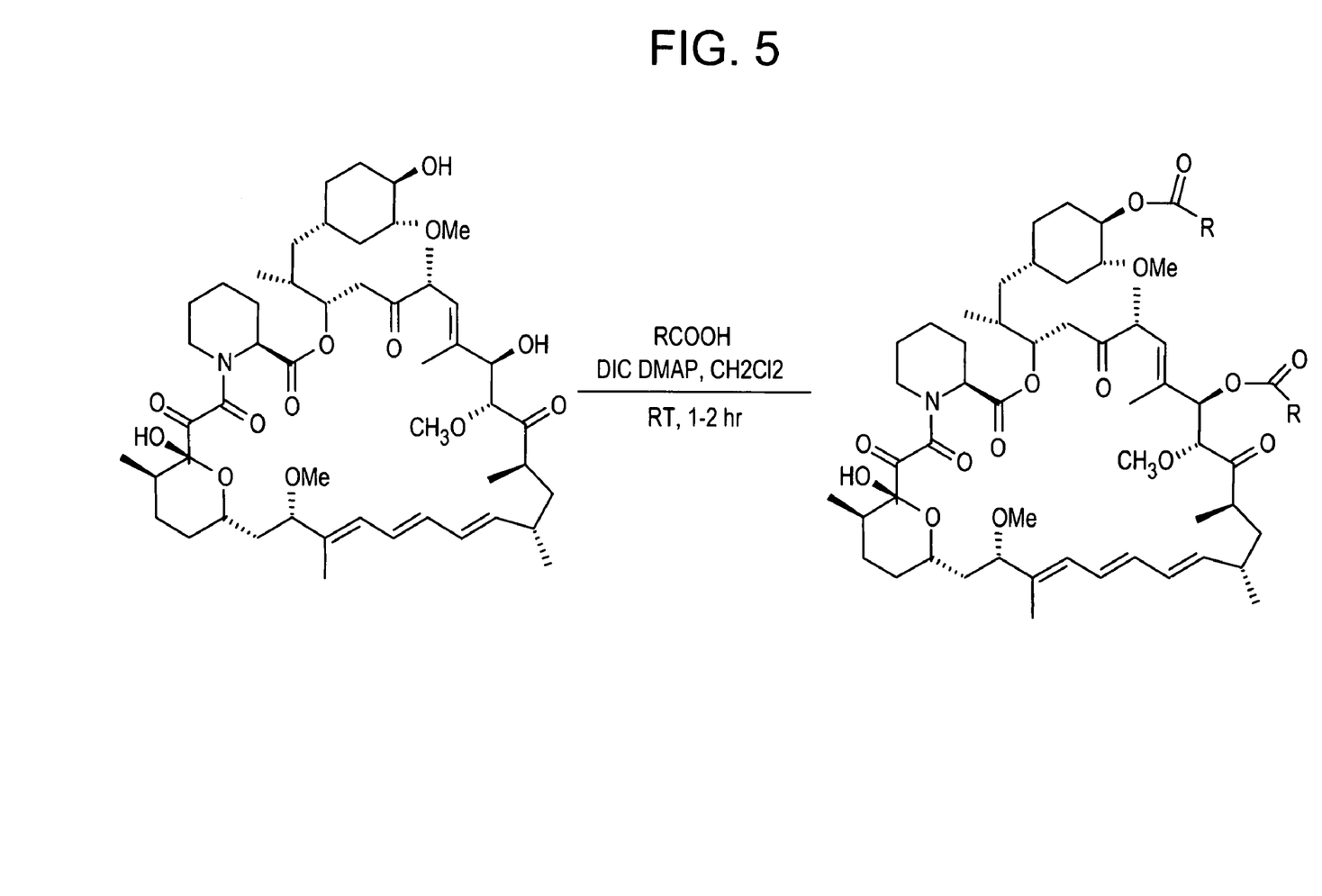
FIG. 5 illustrates an exemplary reaction scheme to introduce one antioxidant moiety each at the 31-, and 42-positions of a rapamycin molecule in accordance with the present invention.

Similarly, reaction conditions may be adjusted to effect a conjugation between rapamycin and RCOOH at both 42- and 31-hydroxyl groups, as shown in scheme illustrated in FIG. 5.

FIG. 5. Reaction scheme for di-substituted rapamycin analog with one antioxidant moiety each at 42- and 31-positions such as commonly known antioxidant functional groups such as conjugated polyunsaturated acids, a phenolic, a triazole, and a tetrazole.

EXAMPLE 1

One exemplary compound of the present invention was synthesized according to the following schemes:

To a suspension of 3-hydroxyphenylacetic acid (1.25 g 0.0082 mol) in 2.5 is mL of dry THF were added thionyl chloride (1 mL, 0.014 mol) and DMF (0.1 mL).

The mixture was stirred at room temperature for 30 to 60 minutes. About 5 mL of acid chloride was thus obtained and ready for use in next step.

To a solution of rapamycin (0.3 g, 0.00033 mol) and 1.2 equivalent of pyridine in dichloromethane (3 mL) was slowly added 1.0 equivalent of above acid chloride over a period of 15 minutes. After finishing the addition, the mixture was stirred at room temperature for about one hour. Then the reaction mixture was put onto a silica gel column. The purification solvent is 1:1 hexanes/ethyl acetate. The first fraction was collected and concentrated in vacuum to give an orange oil (200 mg).

Mass spectrometry confirmed the identity of the target at 1045 Dalton.

Methods of Treatment

The compounds of the present invention, including but not limited to those specified in the examples, possess immunomodulatory activity in mammals (especially humans). As immunosuppressants, the compounds of the present invention are useful for the treatment and prevention of immune-mediated diseases such as the resistance by transplantation of organs or tissue such as heart, kidney, liver, medulla ossium, skin, cornea, lung, pancreas, intestinum tenue, limb, muscle, nerves, duodenum, small-bowel, pancreatic-islet-cell, and the like; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes, uveitis, allergic encephalomyelitis, glomerulonephritis, and the like. Further uses include the treatment and prophylaxis of inflammatory and hyperproliferative skin diseases and cutaneous manifestations of immunologically-mediated illnesses, such as psoriasis, atopic dermatitis, contact dermatitis and further eczematous dermatitises, is seborrhoeis dermatitis, lichen planus, pemphigus, bulious pemphigold, epidermolysis buliosa, urticaria, angioedemas, vasculitides, erythemas, cutaneous eosinophijias, lupus erythematosus, acne and alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, and ocular pemphigus. In addition, reversible obstructive airway disease, which includes conditions such as asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis, and the like are targeted by compounds of the present invention. Inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury, may be treated or prevented by the compounds of the present invention. Other treatable conditions include ischemic bowel diseases, inflammatory bowel diseases, necrotizing enterocolitis, intestinal inflammations/allergies such as Coeliac diseases, proctitis, eosinophilic gastroenteritis, mastocytosis, Crohn's disease and ulcerative colitis; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infarction); intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenesis, metastasis of carcinoma and hypobaropathy; diseases caused by histamine or leukotriene-C.sub.4 release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the present invention may be useful for the treatment and prevention of hepatic disease such as immunogenic diseases (for example, chronic autoimmune liver diseases such as autoimmnune hepatitis, primary biliary cirrhosis and sclerosing cholangitis), partial liver resection, acute liver necrosis (e.g. necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmentation of chemotherapeutic effect, cytomegalovirus infection, particularly HCMV infection, anti-inflammatory activity, sclerosing and fibrotic diseases such as nephrosis, scleroderma, pulmonary fibrosis, arteriosclerosis, congestive heart failure, ventricular hypertrophy, post-surgical adhesions and scarring, stroke, myocardial infarction and injury associated with ischemia and reperfusion, and the like.

Additionally, compounds of the present invention possess FK-506 antagonistic properties. The compounds of the present invention may thus be used in the treatment of immunodepression or a disorder involving immunodepression. Examples of disorders involving immunodepression include AIDS, cancer, fungal infections, senile dementia, trauma (including wound healing, surgery and shock) chronic bacterial infection, and certain central nervous system disorders. The immunodepression to be treated may be caused by an overdose of an immunosuppressive macrocyclic compound, for example derivatives of 12-(2-cyclohexyl-1-methylvinyl)-13,19,21,27-tetramethyl-11,28-dioxa4-azatricyclo [22.3.1.0.sup.4.9]octacos-18-ene such as FK-506 or rapamycin. The overdosing of such medicants by patients is quite common upon their realizing that they have forgotten to take their medication at the prescribed time and may lead to serious side effects.

The ability of the compounds of the present invention to treat proliferative diseases may be demonstrated according to the methods described in Bunchman E T and C A Brookshire, Transplantation Proceed. 23 967-968 (1991); Yamagishi, et al, Biochem. Biophys. Res. Comm. 191 840-846 (1993); and Shichiri, et al., J. Clin. Invest. 87 1867-1871 (1991). Proliferative diseases include smooth muscle proliferation, systemic sclerosis, cirrhosis of the liver, adult respiratory distress syndrome, idiopathic cardiomyopathy, lupus erythematosus, diabetic retinopathy or other retinopathies, psoriasis, scleroderma, prostatic hyperplasia, cardiac hyperplasia, restenosis following arterial injury or other pathologic stenosis of blood vessels. In addition, these compounds antagonize cellular responses to several growth factors, and therefore possess antiangiogenic properties, making them useful agents to control or reverse the growth of certain tumors, as well as fibrotic diseases of the lung, liver, and kidney.

When used to treat restenosis following a balloon angioplasty or stent placement, the compounds of the present invention, and the native rapamycin, are thought to exhibit their therapeutic functions through the inhibition of the mammalian target of rapamycin or mTOR. They may also bind to FKBP receptors.

Aqueous liquid compositions of the present invention are particularly useful for the treatment and prevention of various diseases of the eye such as autoimmune diseases (including, for example, conical cornea, keratitis, dysophia epithelialis corneae, leukoma, Mooren's ulcer, sclevitis and Graves' ophthalmopathy) and rejection of corneal transplantation. These liquid formulations may also be administered through adventitial or perivascular routes to treat restenotic lesions or vulnerable plaque.

When used in the above or other treatments, a therapeutically effective amount of one of the compounds of the present invention may be employed in pure form or, where such forms exist, in pharmaceutically acceptable salt, ester or prodrug form. Alternately, the compound may be administered as a pharmaceutical composition containing the compound of interest in combination with one or more pharmaceutically acceptable excipients. The phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of the present invention administered to a human or lower mammal may range from about 0.01 to about 10 mg/kg/day. For purposes of oral administration, more preferable doses may be in the range of from about 0.001 to about 3 mg/kg/day. If desired, the effective daily dose may be divided into multiple doses for purposes of administration; consequently, single dose compositions may contain such amounts or submultiples thereof to make up the daily dose. Topical administration may involve doses ranging from 0.001 to 3 percent mg/kg/day, depending on the site of application. When administered locally to treat restenosis and vulnerable plaque, the dose may range from about 1 microgram/mm stent length to about 100 microgram/mm stent length.

Pharmaceutical Compositions

The pharmaceutical compositions of the present invention comprise a compound and a pharmaceutically acceptable carrier or excipient, which may be administered orally, rectally, parenterally, intracisternally, intravaginally, intraperitonealry, topically (as by powders, ointments, drops or transdermal patch), bucally, or as an oral or nasal spray. The phrase "pharmaceutically acceptable carrier" means a non-toxic solid, semi-solid or liquid filler, diluent, encapsulating material or formulation auxiliary of any type. The term "parenteral," as used herein, refers to modes of administration which include intravenous, intramuscular, intraperitoneal, intrasternal, subcutaneous and intraarticular injection and infusion.

Pharmaceutical compositions of the present invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternately, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which may be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft, semi-solid and hard-filled gelatin capsules or liquid-filled capsules using such excipients as lactose or milk sugar as well as high molecular weight polyethylene glycols and the like.

The solid dosage forms of tablets, dragees, capsules, pills, and granules may be prepared with coatings and shells such as enteric coatings and other coatings well known in the pharmaceutical formulating art. They may optionally contain opacifying agents and may also be of a composition that they release the active ingredient(s) only, or preferentially, in a certain part of the intestinal tract, optionally, in a delayed manner. Examples of embedding compositions which may be used include polymeric substances and waxes.

The active compounds may also be in a micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions may also include adjuvants such as wetting agents, emulsifying and suspending agents, sweetening, flavoring, and perfuming agents.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar--agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95 percent by weight of the particles of the active ingredient have an effective particle size in the range of 0.01 to 10 micrometers. Compositions for topical use on the skin also include ointments, creams, lotions, and gels.

Alternately, the composition may be pressurized and contain a compressed gas, such as nitrogen or a liquefied gas propellant. The liquefied propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as autoimmune diseases, allergic or inflammatory conditions, and corneal transplants. The compound of the present invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ ciliary, lens, choroid/retina and sclera. The pharmaceutically acceptable ophthalmic vehicle may, for example, be an ointment, vegetable oil or an encapsulating material.

Compositions for rectal or vaginal administration are preferably suppositories or retention enemas which may be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form may contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Compounds of the present invention may also be coadministered with one or more immunosuppressant agents. The immunosuppressant agents within the scope of the present invention include IMURAN.RTM. azathioprine sodium, brequinar sodium, SPANIDIN.RTM. gusperimus trihydrochloride (also known as deoxyspergualin), mizoribine (also known as bredinin), CELLCEPT.RTM. mycophenolate mofetil, NEORAL.RTM. Cylosporin A (also marketed as different formulation of Cyclosporin A under the trademark SANDIMMUNE.RTM.), PROGRAF.RTM. tacrolimus (also known as FK-506), sirolimus and RAPAMUNE.RTM., leflunomide (also known as HWA-486), glucocorticoids, such as prednisolone and its derivatives, antibody therapies such as orthoclone (OKT3) and Zenapax.RTM., and antithymyocyte globulins, such as thymoglobulins.

The local delivery of drug/drug combinations from a stent or other implantable device has the following advantages; namely, the prevention of vessel recoil and remodeling through the scaffolding action of the stent and the prevention of multiple components of neointimal hyperplasia or restenosis as well as a reduction in inflammation and thrombosis. This local administration of drugs, agents or compounds to stented coronary arteries may also have additional therapeutic benefit. For example, higher tissue concentrations of the drugs, agents or compounds may be achieved utilizing local delivery, rather than systemic administration. In addition, reduced systemic toxicity may be achieved utilizing local delivery rather than systemic administration while maintaining higher tissue concentrations. Also in utilizing local delivery from a stent rather than systemic administration, a single procedure may suffice with better patient compliance. An additional benefit of combination drug, agent, and/or compound therapy may be to reduce the dose of each of the therapeutic drugs, agents or compounds, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, anti-thrombotic drugs, agents or compounds.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound having the structure:

wherein only one of R1 or R2 is hydrogen or R3 or both R1 and R2 are R3, and R3 is an unsaturated carbonyl group having the following structure:

n=1 to 10, m=2-10, p=0-4;

or a pharmaceutically acceptable salt thereof.

2. A compound having the structure:

wherein only one of R1 or R2 is hydrogen or both R1 and R2 are R3, or R3, and R3 is:

n=1 to 10, m=2-10;
or a pharmaceutically acceptable salt thereof.

3. A compound having the structure:

wherein only one of R1 or R2 is hydrogen or both R1 and R2 are R3, or R3, and wherein R3 is selected from the group consisting of:

n=1 to n=10
wherein R4 is H.

4. A compound having the structure:

wherein only one of R1 or R2 is hydrogen or both R1 and R2 are R3, and R3 selected from the group consisting of:

, n=1 to n=10
wherein R4 and R5 are hydrogen.

5. A compound having the structure:

wherein only one of R1 or R2 is hydrogen, or R3 or both R1 and R2 are R3, and R3 is n=1 to 10, m=1-10, wherein R6 is wherein R7, R8, R9, R10, R11 are each, independently, a hydroxyl;

or a pharmaceutically acceptable salt thereof.

* * * * *